(12) United States Patent
Loke et al.

(10) Patent No.: US 8,721,651 B2
(45) Date of Patent: May 13, 2014

(54) TEMPLATES AND METHODS

(75) Inventors: Robert M. Loke, Memphis, TN (US); Julien J. Prevost, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 276 days.

(21) Appl. No.: 13/095,275

(22) Filed: Apr. 27, 2011

(65) Prior Publication Data
US 2012/0277809 A1 Nov. 1, 2012

(51) Int. Cl.
*A61B 1/00* (2006.01)
*A61B 5/103* (2006.01)
*A61B 5/117* (2006.01)
*G01B 1/00* (2006.01)

(52) U.S. Cl.
USPC ............................................ 606/102; 33/512

(58) Field of Classification Search
USPC ............ 606/102, 258, 259, 261; 33/512, 262, 33/542.1, 561.1, 712, 783
See application file for complete search history.

(56) References Cited

U.S. PATENT DOCUMENTS

| | | | |
|---|---|---|---|
| 4,931,055 A | 6/1990 | Bumpus et al. | |
| 5,092,866 A | 3/1992 | Breard | |
| 5,330,472 A | 7/1994 | Metz-Stavenhagen | |
| 5,799,407 A | 9/1998 | Powell | |
| 5,938,662 A | 8/1999 | Rinner | |
| 6,051,007 A * | 4/2000 | Hogendijk et al. | 606/151 |
| 6,221,077 B1 | 4/2001 | Rinner et al. | |
| 6,648,891 B2 | 11/2003 | Kim | |
| 6,979,299 B2 | 12/2005 | Peabody et al. | |
| 7,011,658 B2 | 3/2006 | Young | |
| 7,051,451 B2 | 5/2006 | Augostino et al. | |
| 7,166,112 B2 | 1/2007 | Hawkins et al. | |
| 7,290,347 B2 | 11/2007 | Augostino et al. | |
| 7,406,775 B2 | 8/2008 | Funk et al. | |
| 7,476,240 B2 | 1/2009 | Raymond et al. | |
| 7,494,489 B2 | 2/2009 | Roh | |
| 7,674,293 B2 | 3/2010 | Kuiper et al. | |
| 2003/0181920 A1 | 9/2003 | Hawkins et al. | |
| 2006/0195088 A1 | 8/2006 | Sacher et al. | |
| 2007/0079517 A1 | 4/2007 | Augostino et al. | |
| 2007/0173745 A1 | 7/2007 | Diederich et al. | |
| 2007/0239159 A1 | 10/2007 | Altarac et al. | |
| 2008/0039866 A1 | 2/2008 | Stetz et al. | |
| 2008/0147078 A1 | 6/2008 | Francis et al. | |
| 2008/0269767 A1 | 10/2008 | O'Brien | |
| 2008/0287959 A1 | 11/2008 | Quest et al. | |
| 2008/0292161 A1 | 11/2008 | Funk et al. | |
| 2009/0105761 A1 | 4/2009 | Robie | |
| 2009/0182343 A1 | 7/2009 | Trudeau et al. | |
| 2009/0254131 A1 | 10/2009 | Roh | |
| 2010/0106192 A1 | 4/2010 | Barry | |
| 2010/0137913 A1 | 6/2010 | Khatchadourian et al. | |
| 2010/0274287 A1 | 10/2010 | Rouleau et al. | |
| 2010/0274288 A1 * | 10/2010 | Prevost et al. | 606/257 |

FOREIGN PATENT DOCUMENTS

EP 1881794 A2 1/2008

OTHER PUBLICATIONS

U.S. Appl. No. 12/847,080, filed Jul. 30, 2010.

* cited by examiner

*Primary Examiner* — Michael T Schaper
*Assistant Examiner* — David Bates

(57) ABSTRACT

Embodiments of the invention include templates and methods for evaluating the appropriate size and shape for a medical implant. In particular, some embodiments include expandable templates and methods for evaluating appropriate size and shape for implantation of a spinal rod.

20 Claims, 10 Drawing Sheets

TEMPLATES AND METHODS

FIELD OF THE INVENTION

The present invention relates generally to the field of medical implants, and more particularly relates to templates and methods for use in placing a medical implant in a patient.

BACKGROUND

It is known in the prior art to use template devices to measure for appropriate size, shape, and placement of medical implants. However, it may be challenging to implement appropriately sized and shaped templates to match the size and shape of more complex medical implants. Moreover, it may be challenging to achieve such goals without replicating every medical implant that may be used by providing a template for each potential implant. It would be beneficial to provide templates that are capable of having their size and shape changed to match a number of different sizes and shapes of implants. It may also be beneficial to provide templates that may be efficiently disassembled and cleaned.

SUMMARY

An embodiment of the invention is a template having an overall length and configured to evaluate an appropriate size of a spinal rod. The template may have a fixed length section having a first curvilinear shaped portion and a second linear shaped portion and a movable section configured to be moved along the second linear shaped portion to increase and decrease the overall length of the template. The fixed length section and the movable section of the embodiment together define a shape and the overall length of the template.

Another embodiment of the invention is a template having an overall length and configured for use to evaluate an appropriate size for a medical device. The template may include a fixed length section having a first linear shaped portion and a second linear shaped portion and a movable section configured to be moved along the second linear shaped portion to increase and decrease the overall length of the template. The movable section of the embodiment comprises at least two components that are configured to join together to capture at least part of the second linear shaped portion, and the two components are configured to be separated for cleaning after being joined together.

Yet another embodiment of the invention is a method of measuring for the placement of a spinal rod to be placed between a sacrum and one or more lumbar vertebrae with a template. The method may include selecting a hyperlordotic section having a curvilinear shape that fits between a screw attachment structure placed in the sacrum and a screw attachment structure placed in one of the lumbar vertebra. A movable section may be configured to be moved along a segment connected to and extending cranially away from the hyperlordotic section. The method embodiment may also include moving the movable section relative to the hyperlordotic section to configure the template to a size that is estimated to fit with each of the screw attachment structures in the sacrum and the one or more lumbar vertebrae, placing the template into position within each of the screw attachment structures in the sacrum and the one or more lumbar vertebrae, and evaluating the fit of the template within each of the screw attachment structures in the sacrum and the one or more lumbar vertebrae.

DETAILED DESCRIPTION

Figure 1:
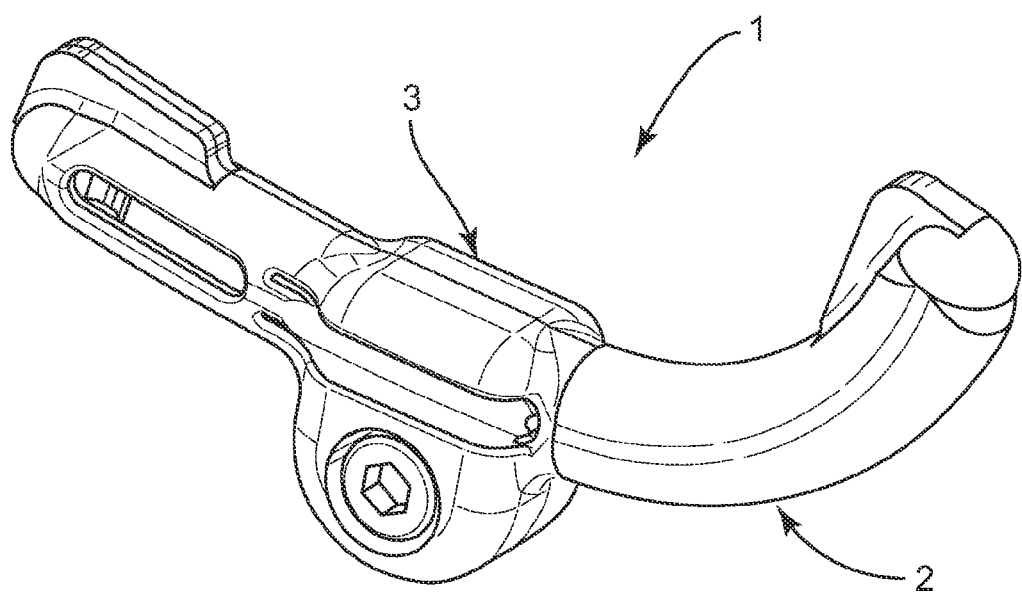
FIG. 1 is a perspective view of an embodiment of a template.
Figure 2:
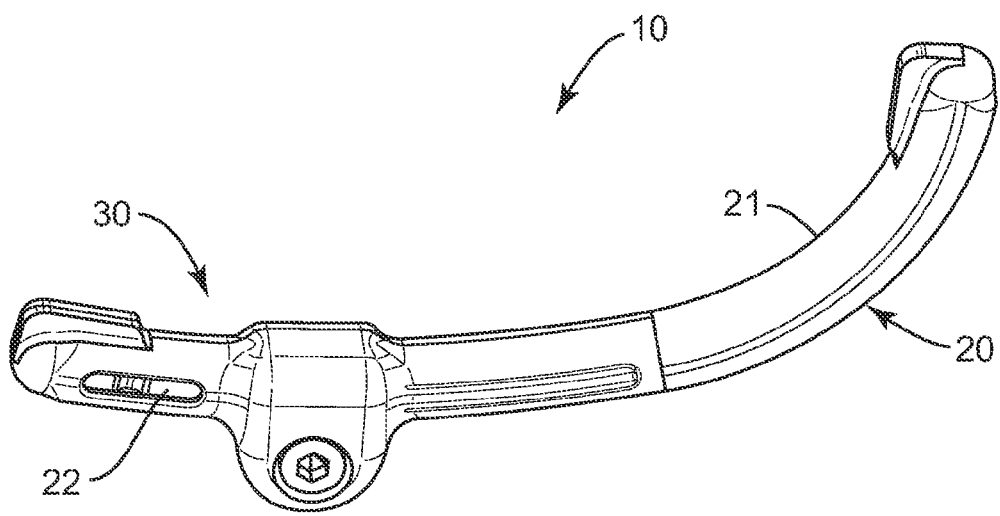
FIG. 2 is a perspective view of an embodiment of a template.
Figure 3:
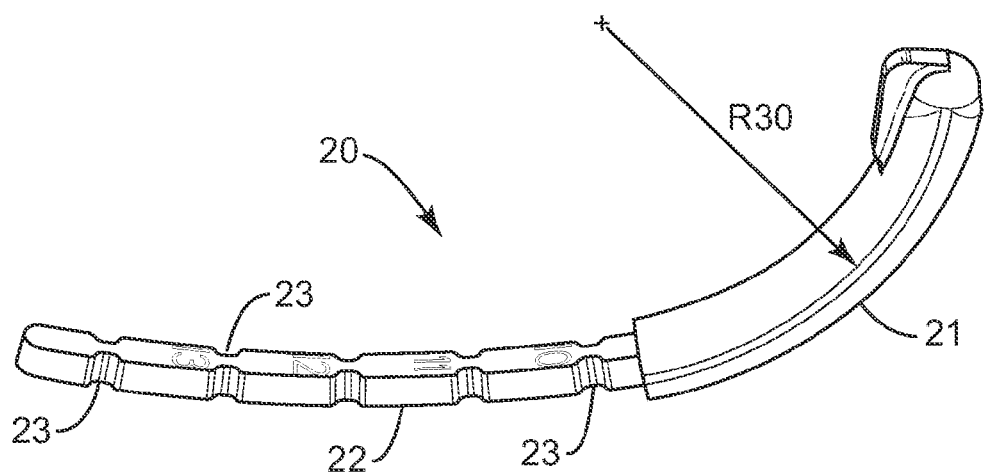
FIG. 3 is a perspective view of a fixed length section of the template of FIG. 2.

A template 1 having an overall length and configured to evaluate an appropriate size of a spinal rod is illustrated in FIG. 1. Evaluation of an appropriate size may also include evaluation of an appropriate shape. The template 1 shown includes a fixed length section 2 having a first curvilinear shaped portion and a second linear shaped portion. The template 1 depicted also includes a movable section 3 configured to be moved along the second linear shaped portion of the fixed length section 2 to increase and decrease the overall length of the template 1. The fixed length section 2 and the movable section 3 together define a shape and the overall length of the template 1. The overall length of the template 1 may be, for example, expandable from 60-80 mm, and lengths and curvatures of the fixed length section 2 and the movable section 3 may be altered for various applications. Lengths and shapes of any functional size or type may be selected to meet design requirements, some of which will be detailed herein.

Another embodiment of a template 10 is illustrated in FIGS. 2-7 and 9-11C. The template 10 has an overall length and is configured to evaluate an appropriate size of a spinal rod that may be implanted in the evaluated area. Evaluation of an appropriate size may also include evaluation of an appropriate shape. The template 10 shown includes a fixed length section 20 having a first linear shaped portion 21 and a second linear shaped portion 22. The fixed length section 20 is illustrated in more detail in FIG. 3. The first linear shaped portion 21 illustrated is curvilinear. In the embodiment shown, the first linear shaped portion 21 includes a segment shaped along an approximately 30 mm radius (labeled R30). In other embodiments, a first linear shaped portion includes a radius of curvature, or at least a segment with a radius of curvature, of about 15 mm to 35 mm. Another embodiment of a first linear shaped portion includes a segment shaped along an approximately 20 mm radius. Another embodiment of a first linear shaped portion includes a segment shaped along an approximately 127 mm radius, for example, to approximately match a typical spinal curvature at some spinal segments. A first linear shaped portion of some embodiments may be straight, may include parts that are straight, parts that are curved, multiple or compound curves, combinations of straight and curved parts, or any other beneficial or effective shape. The second linear shaped portion 22 of the illustrated embodiment includes a radius of curvature greater than the radius of curvature of the first linear shaped portion 21. A second linear shaped portion of some embodiments may be straight, may include parts that are straight, parts that are curved, multiple or compound curves, combinations of straight and curved parts, or any other beneficial or effective shape.

Figure 8:
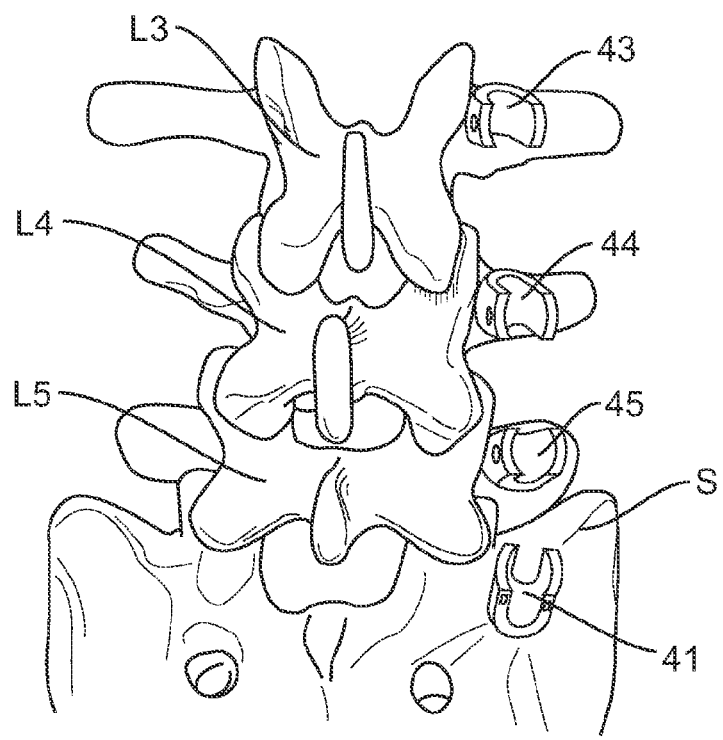
FIG. 8 is a perspective view of a lumbosacral spinal segment in which screw attachment structures have been implanted.
Figure 9:
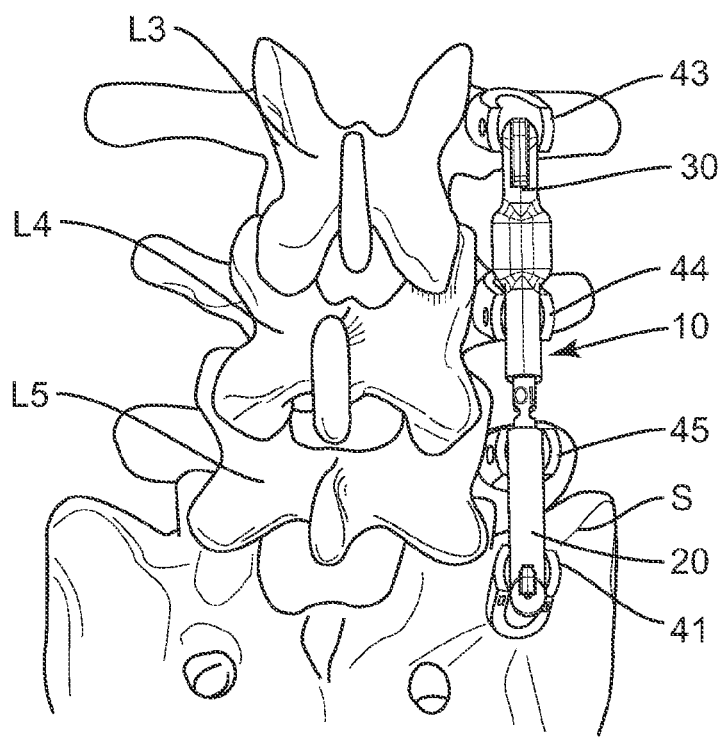
FIG. 9 is a perspective view of a lumbosacral spinal segment with screw attachment structures in which a template has been placed.
Figure 10:
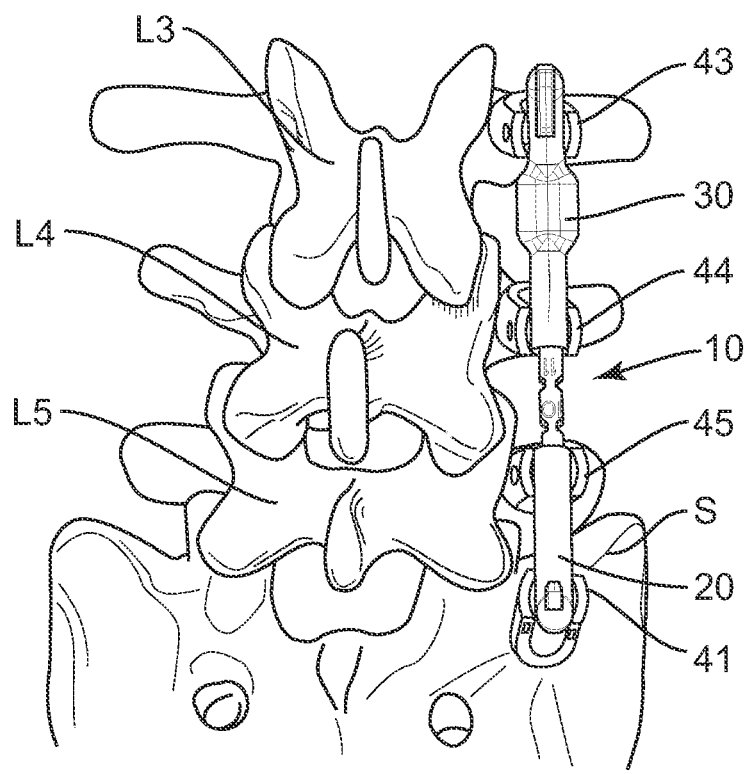
FIG. 10 is a perspective view of a lumbosacral spinal segment with screw attachment structures in which a template has been placed.
Figure 11A:
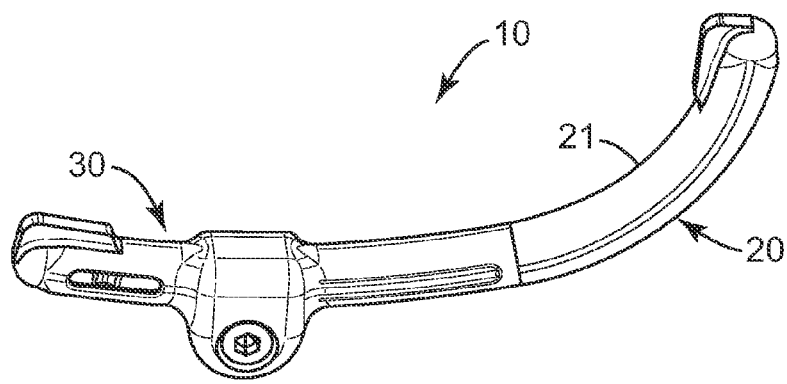
FIGS. 11A-11C show perspective views of the template of FIG. 2 in different states of movement.
Figure 11B:
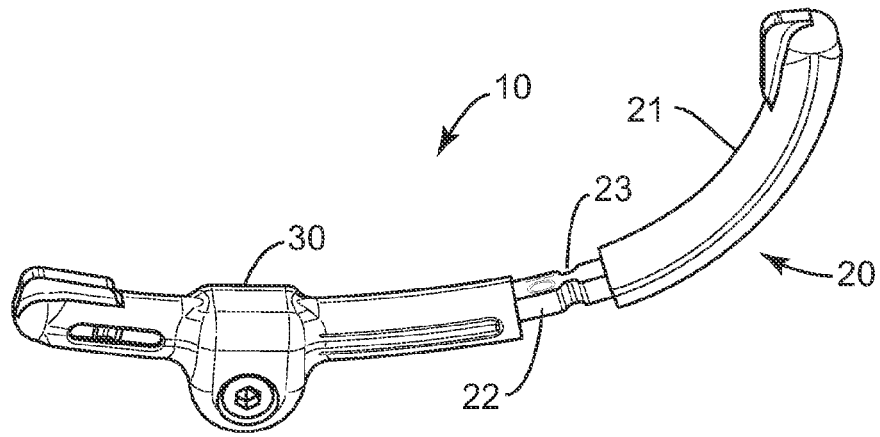
Figure 11C:
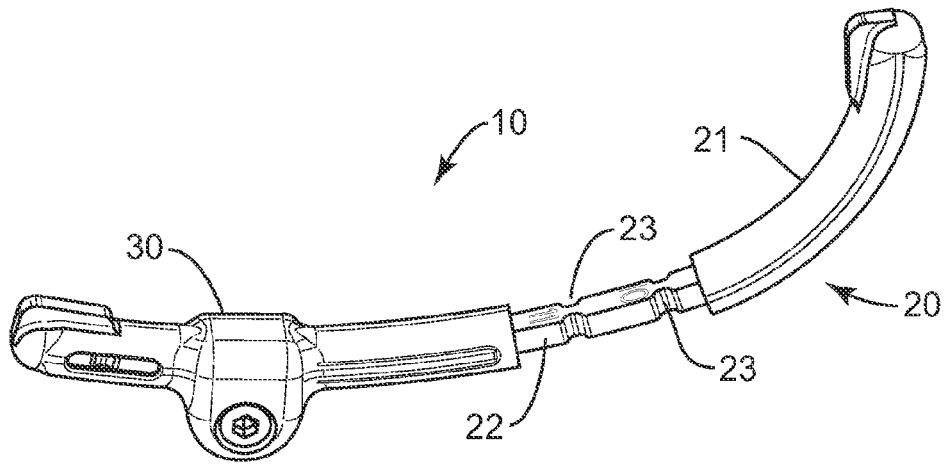

A first linear shaped portion of some embodiments of the fixed length section 20 is configured to fit at least between screw attachment structures implanted in a spine. As used herein, the term "screw attachment structure" includes structures such as, spinal screws, spinal hooks and other devices of any variety that attach to a patient's anatomy. For example, as illustrated in FIGS. 8-10 a screw attachment structure 41 has been placed in a sacrum S, and a screw attachment structure 45 has been placed in a lumbar vertebra L5. As illustrated in FIGS. 9 and 10, the fixed length section 20 of the template 10 has been placed between the attachment structures 41, 45. In the illustrated embodiment, the fixed length section 20 is shaped to fit between a hyperlordotic curvature, as exists between a sacrum and an L5 vertebra. A hyperlordotic curvature may encompass any curvature greater than a typical lordotic curvature, including but not limited to, the sacrum to L5 junction, a deformity, or an injury. A set of templates may include two or more fixed length sections for use in measuring for placement of a medical device, such as a spinal rod. Each fixed length section may be joined with one or more different movable sections. The fixed length section 20 illustrated in FIG. 3, includes indents 23 in the second linear shaped portion 22. The fixed length section 20 shown also includes sizing indicators to inform a user of the length to which the template 10 has been expanded. As shown, the sizing indicators 9, 10, 11, 12, and 13 inform a user of the overall length of the template 10 based on the largest indicator shown in a state of expansion. In the illustrated embodiment, each indicator must be multiplied by 10 mm to properly reflect the overall length of the template 10, and subsequent spinal rod. For example, if the indicator 11 were the largest indicator showing in a state of expansion, the overall length of the template 10 would be 110 mm.

Figure 4:
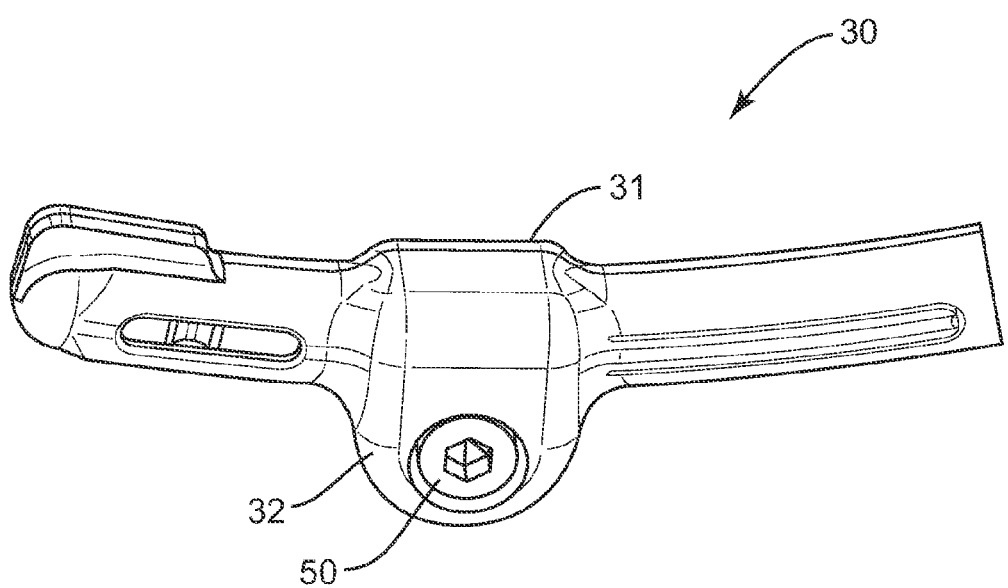
FIG. 4 is a perspective view of a movable section of the template of FIG. 2.
Figure 5:
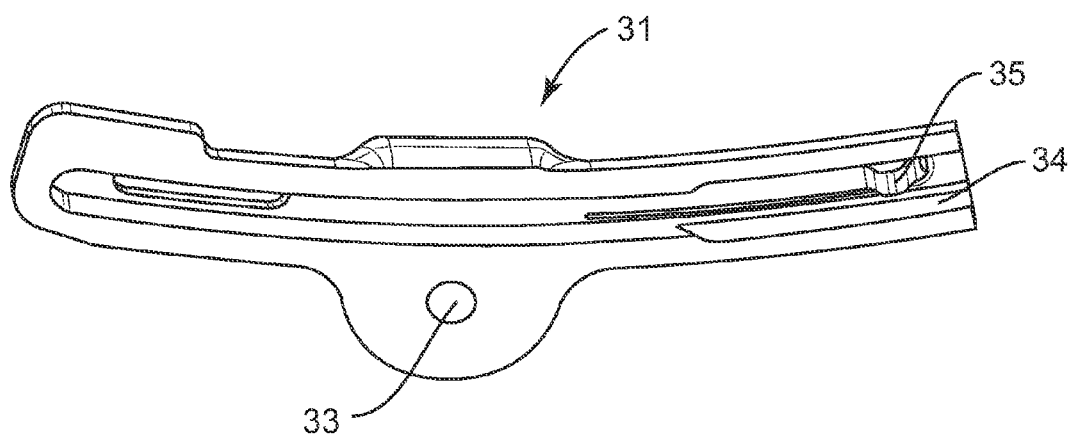
FIG. 5 is a perspective view of one of the components the movable section of FIGS. 4 and 6.
Figure 6:
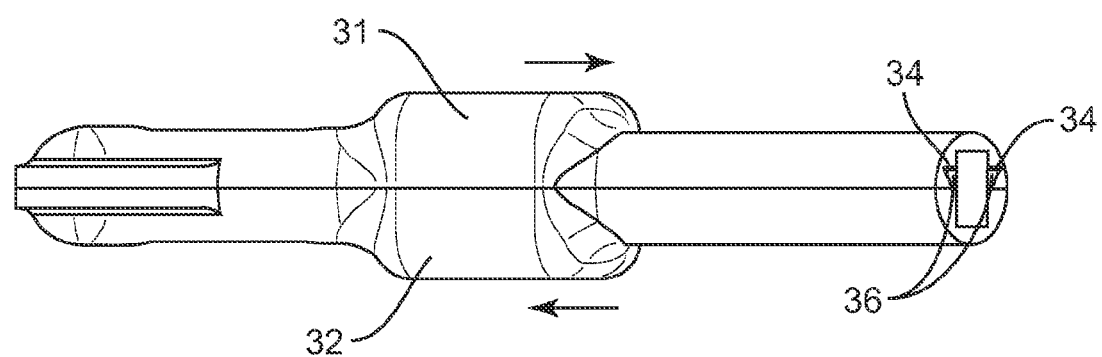
FIG. 6 is a perspective view of the movable section of the template of FIG. 2.
Figure 7:
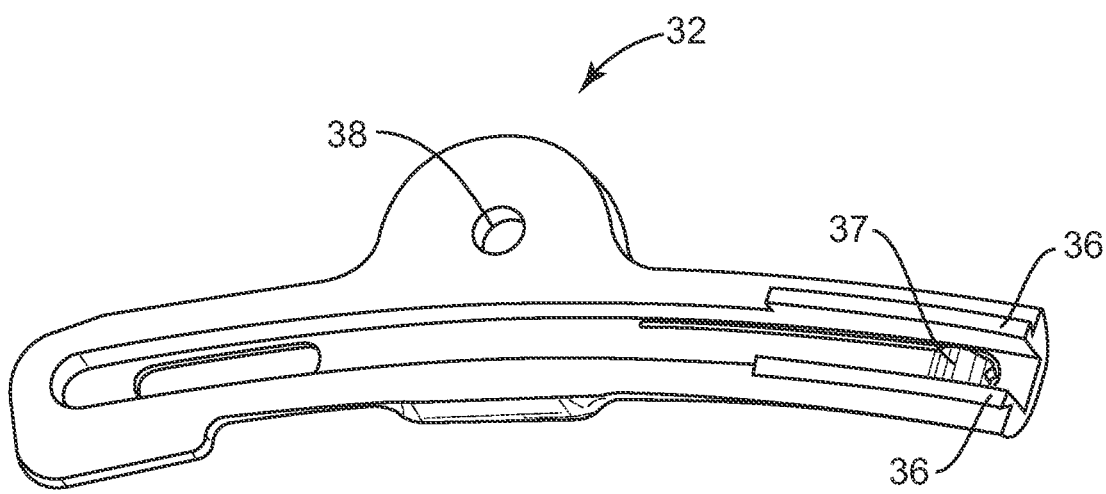
FIG. 7 is a perspective view of one of the components the movable section of FIGS. 4 and 6.

The template 10 depicted also includes a movable section 30 configured to be moved along the second linear shaped portion 20 to increase and decrease the overall length of the template 10. As shown in FIG. 4, the movable section 30 includes first and second components 31, 32. The first and second components 31, 32 are shown joined together in part by a fastener 50. As illustrated in FIG. 5, the first component 31 of the movable section 30 includes a hole 33 through which the fastener 50 may be placed. The first component 31 also includes a first tab 35 and a first interdigitating portion 34. The first tab 35 illustrated is a device that is biased toward the center of the movable section 30 and includes a rounded key that is designed to couple into the indents 23 when the template 10 is assembled. As illustrated in FIGS. 5 and 6, the first interdigitating portion 34 is a slot for receiving a dovetail shaped, second interdigitating portion 36 from the second component 32. As illustrated in FIG. 7, the second component 32 of the movable section 30 includes a hole 38 through which the fastener 50 may be placed. The second component 32 also includes a second tab 37 and the second interdigitating portion 36. The second tab 37 illustrated is a device that is biased toward the center of the movable section 30 and includes a rounded key that is designed to couple into the indents 23 when the template 10 is assembled. As illustrated in FIGS. 6 and 7, the second interdigitating portion 36 is dovetail shaped and configured to be received in the first interdigitating portion 34 of the first component 31.

First and second interdigitating portions of various embodiments may be of any functional shape or characteristic to assist in the joining together of at least part of portions of two components. In the illustrated embodiment, the interdigitating portions are shaped as a dovetail connection, but in other embodiments the interdigitating portions may be a dado, pin, lap, half-lap, dowel, partial dowel, inclined plane, thread, or any other functional connection type. In the illustrated embodiment, the first and second components 31, 32 are separated and joined by a linear sliding action relative to the longitudinal axes of the first and second components 31, 32 after removal of the fastener 50. Arrows depicting the relative linear sliding motion between the first and second components 31, 32 are provided in FIG. 6. In other embodiments first and second components may be separated and joined by any linear, rotational, or combination force that is effective to actuate the design. Some embodiments may not include a fastener such as the fastener 50 or may include multiple fasteners.

The first and second components 31, 32 of the movable section 30 illustrated are configured to join together to capture at least part of the second linear shaped portion 22, as illustrated in FIGS. 2 and 11A-11C. The movable section 30 illustrated includes substantially the same linear shape as the second linear shaped portion 22. In the embodiment illustrated, this shape allows for the movable section 30 to be moved along the second linear shaped portion 22 at a common radius of curvature. Other embodiments may include different but compatible shapes to enable movement, such as but not limited to, a straight linear shape. The first and second components 31, 32 of the illustrated embodiment may be separated for cleaning between and within the components. The embodiment shown permits separation of components to reduce or eliminate the number of inaccessible reentrant volumes that may restrict thorough cleaning.

Some embodiments of the movable section 30 are configured to be placed in two screw attachment structures that have been implanted in lumbar vertebrae of a spine. For example, as illustrated in FIGS. 8-10, screw attachment structures 43, 44 have been placed in lumbar vertebra L3, L4 respectively. As illustrated in FIGS. 9 and 10, the movable section 30 of the template 10 has been placed between the attachment structures 43, 44. In the illustrated embodiment, the movable section 30 is shaped to fit between vertebrae with a lordotic curvature. In some embodiments, a movable section may only contact one screw attachment structure or may contact more than two screw attachment structures. A set of templates may include two or more movable sections for use in measuring for placement of a medical device, such as a spinal rod. Each movable section may be joined with one or more different fixed length sections. In some spinal rod template embodiments, templates, in whole or in part, including fixed length sections or movable sections, may be for use in measuring between vertebrae that are not adjacent to one another. Intermediate attachment structures may not be present because no attachment structure is present or because one or more intermediate vertebrae have been removed.

The fixed length section 20 and the movable section 30 together define a shape and the overall length of the template 10. The overall length of the template 10 may be, for example, expandable from 90-130 mm, and lengths and curvatures of the fixed length section 20 and the movable section 30 may be altered for various applications. Lengths and shapes of any functional size or type may be selected.

Various embodiments of a template, wholly or its components individually, may be made from any biocompatible material. For example and without limitation, biocompatible materials may include in whole or in part: non-reinforced polymers, reinforced polymers, metals, ceramics and combinations of these materials. Reinforcing of polymers may be accomplished with carbon, metal, or glass fibers or any other effective fiber material. In some embodiments, biocompatible materials may include sections of bone or other tissues. Tissue materials include, but are not limited to, autograft, allograft, or xenograft. Examples of biocompatible polymer materials include polyethylene, low density polyethylene, polymethylmethacrylate (PMMA), polyetheretherketone (PEEK), polyetherketoneketone (PEKK), and polyurethane. A biocompatible polymer may also include a polymeric hydroxyethylmethacrylate (PHEMA). Example biocompatible metals include stainless steel and other steel alloys, cobalt chrome alloys, tantalum, titanium, titanium alloys, titanium-nickel alloys such as Nitinol and other superelastic or shape-memory metal alloys.

An embodiment of the invention is a method of measuring for the placement of a spinal rod to be placed between a sacrum and one or more lumbar vertebrae with a template. Elements of method embodiments described herein are discussed with reference to FIGS. 8-11C. An act of some method embodiments includes selecting a hyperlordotic section having a curvilinear shape that fits between a screw attachment structure placed in the sacrum and a screw attachment structure place in one of the lumbar vertebra. In the illustrated embodiment, the hyperlordotic section with a curvilinear shape is the first linear shaped portion 21 of the fixed length section 20. This hyperlordotic section is shown fitted between multi-axial, top-loading pedicle screw receiver heads or so-called tulip components that have been placed in a sacrum S and the L5 lumbar vertebra. Any other functional screw attachment structure may be used, such as but not limited to three-dimensional screws, side-loading screws, spinal hooks, and other devices of any variety that attach to a patient's anatomy. In the illustrated case, the hyperlordotic section fits properly (FIGS. 9 and 10), but if the hyperlordotic section did not fit, a different hyperlordotic section could be selected.

In the illustrated embodiment, the movable section 30 is configured to be moved along a segment that extends cranially from the hyperlordotic section. That is, in this case, the movable section 30 moving along the second linear shaped section 22 of the fixed length or hyperlordotic section. The term "cranially" as used herein is intended to mean toward the head of a patient when the template 10 is in position on a spine of a patient.

Another act of some method embodiments is to move the movable section 30 relative to the hyperlordotic section to configure the template 10 to a size that is estimated to fit with each of the screw attachment structures in the sacrum and the one or more lumbar vertebrae. The template 10 may be placed into position within each of the screw attachment structures in the sacrum and the one or more lumbar vertebrae, as shown in FIG. 9, for example.

Another act of some method embodiments includes evaluating the fit of the template within each of the screw attachment structures in the sacrum and the one or more lumbar vertebrae. For example, as shown in FIG. 9, the fit of the template 10 in the attachment structures 41, 43, 44, and 45 is evaluated. The template 10 appears to fit well within each of the attachment structures except attachment structure 43. Therefore, from this evaluation, it is determined that an implant larger than the template 10, as adjusted in FIG. 9, is needed. If the fit of the template 10 in the attachment structures would have been proper for all attachment structures, then a size corresponding to an implant to be used could have been read from the template 10, and an appropriately sized spinal rod for implantation could have been selected.

Some method embodiments include, as is the case with the present example, determining that the template 10 does not fit with each of the screw attachment structures 41, 43, 44, and 45 in the sacrum and the one or more lumbar vertebrae, adjusting the size of the template 10, and placing the template 10 into position within each of the screw attachment structures 41, 43, 44, and 45 in the sacrum and the one or more lumbar vertebrae. The adjusted size is illustrated in the present example in the expanded state of the template 10 in FIGS. 10 and 11C. The fit of the template 10 may be evaluated within each of the screw attachment structures 41, 43, 44, and 45 in the sacrum and the one or more lumbar vertebrae, as depicted in FIG. 10. The fit of the template 10 appears proper for all attachment structures, therefore a size corresponding to an implant to be used may be read from the template 10, and an appropriately sized spinal rod for implantation may be selected. The size of the template 10 is determined by observing the largest indicator shown in a state of expansion, which is 11 in FIGS. 10 and 11C. The indicator is multiplied by 10 mm to properly reflect the overall length of the template 10, which is 110 mm in this case.

Method embodiments may also include placing a rod within each of the screw attachment structures in the sacrum and the one or more lumbar vertebrae that corresponds with the size of the template that has been evaluated to fit with each of the screw attachment structures in the sacrum and the one or more lumbar vertebrae. In the example case, a spinal rod of 110 mm overall length and having a shape corresponding to the template evaluated would be placed. In other embodiments, offsets or approximations may be used when evaluating the fit of a template to determine a final implant size.

Another embodiment of the invention is a method of cleaning a template having an overall length and configured for use to evaluate an appropriate size for a medical device. The method may include providing a fixed length section having a first linear shaped portion and a second linear shaped portion, and a movable section configured to be moved along the second linear shaped portion to increase and decrease the overall length of the template. In some embodiments, the movable section comprises at least two components that are configured to join together to capture at least part of the second linear shaped portion. The method may include removing the second linear shaped portion from the movable section and separating the at least two component of the movable section from one another. The two components of some embodiments are subsequently cleaned before rejoining and assembling the movable section and the fixed length section.

Terms such as side, top, and the like have been used relatively herein. However, such terms are not limited to specific coordinate orientations, but are used to describe relative positions referencing particular embodiments. Such terms are not generally limiting to the scope of the claims made herein. Any embodiment or feature of any section, portion, or any other component shown or particularly described in relation to various embodiments of similar sections, portions, or components herein may be interchangeably applied to any other similar embodiment or feature shown or described herein.

While embodiments of the invention have been illustrated and described in detail in the disclosure, the disclosure is to be considered as illustrative and not restrictive in character. All changes and modifications that come within the spirit of the invention are to be considered within the scope of the disclosure.

What is claimed is:

1. A template having an overall length and configured to evaluate an appropriate size of a spinal rod comprising:
a fixed length section having a first curvilinear shaped portion and a second linear shaped portion comprising a plurality of spaced apart indents that each extend perpendicular to an axis defined by the fixed length section, the second linear shaped portion comprising numerical sizing indicators between adjacent indents; and
a movable section telescopically connected to the second linear shaped portion and configured to be moved along a longitudinal axis of the second linear shaped portion to increase and decrease the overall length of the template, the movable section comprising opposite first and second tabs that are each biased to a center of the movable section and include a rounded key that couples into a respective indent;
wherein the fixed length section and the movable section together define a shape and the overall length of the template, wherein a respective one of the sizing indicators represents the overall length of the implant.

2. The template of claim 1 wherein the first curvilinear shaped portion of the fixed length section includes a radius of curvature of about 15 mm to 35 mm.

3. The template of claim 1 wherein the first curvilinear shaped portion of the fixed length section is fit at least between a screw attachment structure configured to be placed in a sacrum and a screw attachment structure configured to be placed in a lumbar vertebra.

4. The template of claim 3 wherein the curvilinear shaped portion of the fixed length section is shaped to fit a hyperlordotic curvature.

5. The template of claim 1 wherein the second linear shaped portion is curved.

6. The template of claim 1 wherein the second linear shaped portion is straight.

7. The template of claim 1 wherein the movable section includes substantially the same linear shape as the second linear shaped portion.

8. The template of claim 1 wherein the movable section is placed in two screw attachment structures that are configured to be implanted, respectively in two lumbar vertebra.

9. The template of claim 1 wherein the movable section comprises two components that are configured to join together to capture at least part of the second linear shaped portion, one of the components including the first tab of the movable section and the other component comprising the second tab of the movable section.

10. The template of claim 1 wherein the respective one of the sizing indicators is multiplied by 10 mm to provide the overall length of the template.

11. The template of claim 1 wherein:
the movable section comprises a first end including an inner surface defining a passage that includes the first and second tabs; and
the movable section comprises a second end opposite the first end that terminates at an end face that faces away from the first curvilinear shaped portion.

12. A template having an overall length and configured for use to evaluate an appropriate size for a medical device comprising:
a fixed length section having a first linear shaped portion and a second linear shaped portion comprising a plurality of spaced apart indents that each extend perpendicular to an axis defined by the fixed length section, the second linear shaped portion comprising numerical sizing indicators between adjacent indents; and
a movable section telescopically connected to the second linear shaped portion and configured to be moved along a longitudinal axis of the second linear shaped portion to increase and decrease the overall length of the template, wherein a respective one of the sizing indicators represents the overall length of the implant, the movable section comprising opposite first and second tabs that are each biased to a center of the movable section and include a rounded key that couples into a respective indent;
wherein the movable section comprises two components, one of the components including the first tab and the other component comprising the second tab, the two components being configured to be separated for cleaning after being joined together.

13. The template of claim 12 wherein the first linear shaped portion of the fixed length section is curvilinear.

14. The template of claim 13 wherein the first linear shaped portion of the fixed length is fit between a screw attachment structure configured to be placed in a sacrum and a screw attachment structure configured to be placed in a lumbar vertebra.

15. The template of claim 12 wherein the two components of the movable section are joined together at least in part by a fastener.

16. The template of claim 12 wherein the two components of the movable section are joined together at least in part by portions of the two components that interdigitate.

17. The template of claim 12 wherein the two components of the movable section are separated by sliding the two components substantially along longitudinal axes defined by the two components.

18. The template of claim 12 wherein the fixed length section and the movable section together define a shape and the overall length of the template.

19. A method of measuring for the placement of a spinal rod to be placed between a sacrum and one or more lumbar vertebrae with a template comprising:
providing a template, the template having an overall length and configured to evaluate an appropriate size of a spinal rod, the template comprising:
a fixed length section having a first curvilinear shaped portion and a second linear shaped portion comprising a plurality of spaced apart indents that each extend perpendicular to an axis defined by the fixed length section, the second linear shaped portion comprising numerical sizing indicators between adjacent indents; and
a movable section telescopically connected to the second linear shaped portion and configured to be moved along a longitudinal axis of the second linear shaped portion to increase and decrease the overall length of the template, the movable section comprising opposite first and second tabs that are each biased to a center of the movable section and include a rounded key that couples into a respective indent;
wherein the fixed length section and the movable section together define a shape and the overall length of the template, wherein a respective one of the sizing indicators represents the overall length of the implant;
wherein the fixed length section has a curvilinear shape that fits between a screw attachment structure placed in the sacrum and a screw attachment structure placed in one of the lumbar vertebra, wherein the movable section is configured to be moved along a segment connected to and extending cranially away from the fixed length section;

moving the movable section relative to the fixed length section to configure the template to a size that is estimated to fit with each of the screw attachment structures in the sacrum and the one or more lumbar vertebrae;

placing the template into position within each of the screw attachment structures in the sacrum and the one or more lumbar vertebrae; and evaluating the fit of the template within each of the screw attachment structures in the sacrum and the one or more lumbar vertebrae.

20. The method of claim 19, further comprising reading a size corresponding to an implant from the template and selecting a spinal rod for implantation.

* * * * *